US011142935B2

(12) United States Patent
Bae et al.

(10) Patent No.: US 11,142,935 B2
(45) Date of Patent: Oct. 12, 2021

(54) SLIDING STOP SWITCH AND WEARABLE CHAIR INCLUDING THE SAME

(71) Applicants: HYUNDAI MOTOR COMPANY, Seoul (KR); KIA MOTORS CORPORATION, Seoul (KR)

(72) Inventors: Ki Hyeon Bae, Yongin-si (KR); Kyung Mo Jung, Seongnam-si (KR); Kyu Jung Kim, Seoul (KR); Ju Young Yoon, Suwon-si (KR); Dong Jin Hyun, Suwon-si (KR)

(73) Assignees: HYUNDAI MOTOR COMPANY, Seoul (KR); KIA MOTORS CORPORATION, Seoul (KR)

( * ) Notice: Subject to any disclaimer, the term of this patent is extended or adjusted under 35 U.S.C. 154(b) by 126 days.

(21) Appl. No.: 16/533,066

(22) Filed: Aug. 6, 2019

(65) Prior Publication Data

US 2020/0165855 A1    May 28, 2020

(30) Foreign Application Priority Data

Nov. 22, 2018   (KR) .......................... 10-2018-0145358

(51) Int. Cl.
*A47C 7/00*    (2006.01)
*E05F 5/00*    (2017.01)
(Continued)

(52) U.S. Cl.
CPC ............. *E05F 5/003* (2013.01); *B25J 9/0006* (2013.01); *A47C 3/00* (2013.01); *A47C 7/68* (2013.01);
(Continued)

(58) Field of Classification Search
CPC ...... A61F 5/0106; A61F 5/0125; A47C 9/025; A47C 9/10; A47C 7/68; B25J 9/0006;
(Continued)

(56) References Cited

U.S. PATENT DOCUMENTS 2,173,569 A * 9/1939 Troendle ................ B60N 3/004
 297/146
4,138,156 A   2/1979 Bonner
(Continued)

FOREIGN PATENT DOCUMENTS

CN    104970607 A    10/2015
CN    106859122 A    6/2017
(Continued)

OTHER PUBLICATIONS

U.S. Office Action dated Sep. 23, 2020 issued in U.S. Appl. No. 16/533,084.
(Continued)

*Primary Examiner* — Syed A Islam
(74) *Attorney, Agent, or Firm* — Morgan, Lewis & Bockius LLP

(57) ABSTRACT

A sliding stop switch may include a first rod extending in the longitudinal direction thereof, a second rod coupled to the first rod such that one end portion thereof is slidable in the longitudinal direction of the first rod, and a switch member coupled to the first rod to slide in the longitudinal direction of the first rod and to be fixed at a plurality of points on the first rod to stop the sliding of one end portion of the second rod.

14 Claims, 6 Drawing Sheets

(51) Int. Cl.

| | |
|---|---|
| *B25J 9/00* | (2006.01) |
| *A47C 9/00* | (2006.01) |
| *A47C 3/00* | (2006.01) |
| *B25J 13/02* | (2006.01) |
| *B60N 3/00* | (2006.01) |
| *A47D 1/00* | (2006.01) |
| *A61F 5/01* | (2006.01) |
| *A47C 7/68* | (2006.01) |
| *A61G 5/10* | (2006.01) |
| *A61G 5/14* | (2006.01) |
| *A47C 9/02* | (2006.01) |

(52) U.S. Cl.
CPC .............. *A47C 9/002* (2013.01); *A47C 9/025* (2013.01); *A47D 1/004* (2013.01); *A61F 5/0106* (2013.01); *A61G 5/1067* (2013.01); *A61G 5/14* (2013.01); *B25J 13/02* (2013.01); *B60N 3/004* (2013.01)

(58) Field of Classification Search
CPC ........ A61G 5/14; A61G 5/1067; B60N 3/004; A47D 1/004; E05F 5/003
USPC .................................................. 297/256.11
See application file for complete search history.

(56) References Cited

U.S. PATENT DOCUMENTS 10,271,660 B2    4/2019   Gunura et al.
2013/0320725 A1* 12/2013  Conway ............... B60N 2/2863
                                                297/256.11
2019/0225131 A1*  7/2019  Bellamy ................. B60R 11/02
2020/0155390 A1*  5/2020  Bae ......................... A47C 9/025

FOREIGN PATENT DOCUMENTS

| CN | 107252210 A      |   | 10/2017 |             |
|----|------------------|---|---------|-------------|
| JP | 5883256 B2       |   | 3/2016  |             |
| JP | 6107722 B2       |   | 4/2017  |             |
| KR | 10-0690645 B1    |   | 3/2007  |             |
| KR | 20-2008-0004603 U |  | 10/2008 |             |
| KR | 20-0471438 Y1    |   | 2/2014  |             |
| KR | 10-1500200 B1    |   | 3/2015  |             |
| KR | 10-2015-0146169 A |  | 12/2015 |             |
| KR | 10-2016-0007456 A |  | 1/2016  |             |
| KR | 10-2017-0006632 A |  | 1/2017  |             |
| KR | 10-2017-0036894 A |  | 4/2017  |             |
| KR | 10-2017-0060783 A |  | 6/2017  |             |
| KR | 10-1755806 B1    |   | 7/2017  |             |
| KR | 10-2018-0083336 A |  | 7/2018  |             |
| KR | 20200059360 A    | * | 5/2020  | ............. A47C 9/025 |
| WO | 2017/067705 A1   |   | 4/2017  |             |
| WO | 2017/067706 A1   |   | 4/2017  |             |

OTHER PUBLICATIONS

International Search Report dated Aug. 1, 2019 issued in International Patent Application No. PCT/KR2019/000518.
International Search Report dated Aug. 1, 2019 issued in International Patent Application No. PCT/KR2019/002151.

* cited by examiner

SLIDING STOP SWITCH AND WEARABLE CHAIR INCLUDING THE SAME

CROSS-REFERENCE TO RELATED APPLICATION

The present application claims priority to Korean Patent Application No. 10-2018-0145358, filed on Nov. 22, 2018, the entire contents of which is incorporated herein for all purposes by this reference.

BACKGROUND OF THE INVENTION

Field of the invention

The present invention relates to a sliding stop switch and a wearable chair including the same, and more particularly to a structure in which a switch member is disposed between rods to slide along one of the rods to stop the rotation of the rods relative thereto.

Description of Related Art

In recent years, research has been actively conducted into a multi-purpose wearable robot which may be used to assist handicapped people or the old and the weak in moving or to rehabilitate muscular dystrophy patients in the medical field, to assist soldiers in easily bearing heavy soldiers' kits in the military field, and to assist workers in easily carrying heavy loads in industrial fields.

In general, a wearable robot is manufactured by organically coupling links, which are configured to perform joint actions similar to those of human beings, into a shape that a user can wear. In the case in which a user wears a wearable robot, the wearable robot supplements the physical strength of the thigh or the lower leg of the user such that the user can perform high-load work requiring force beyond the general physical strength limits of human beings without the help of an additional external device.

However, an active type wearable robot, which is power-driven to supplement the physical strength of human beings, is relatively heavy, and needs to be controlled using a controller, which is complicated. As a result, the stability of the present type of wearable robot is low, and the sitting angle of the present type of wearable robot is limited.

Therefore, there is a necessity for a passive type wearable chair which is capable of supporting a heavy load while being lightweight. In a conventional wearable chair, however, it is difficult to change the sitting angle of the wearable chair. Consequently, it is necessary to provide a structure in which a switch member for stopping sliding may be moved and then fixed when a user sits down.

The information included in this Background of the Invention section is only for enhancement of understanding of the general background of the invention and may not be taken as an acknowledgement or any form of suggestion that this information forms the prior art already known to a person skilled in the art.

BRIEF SUMMARY

Various aspects of the present invention are directed to providing a sliding stop switch that enables a user to easily move a switch member for stopping sliding and a wearable chair including the same, wherein the sitting angle of the chair is variable.

In accordance with an aspect of the present invention, the above and other objects may be accomplished by the provision of a sliding stop switch including a first rod extending in the longitudinal direction thereof, a second rod coupled to the first rod such that one end portion thereof is slidable in the longitudinal direction of the first rod, and a switch member coupled to the first rod to slide in the longitudinal direction of the first rod and to be fixed at a plurality of points on the first rod to stop the sliding of one end portion of the second rod.

The first rod may be located on the second rod or the switch member to surround opposite side surfaces and a portion of the lower surface of the second rod or the switch member.

The switch member may be provided at one side thereof with a coupling protrusion, which protrudes toward the first rod, and the first rod may be provided at a plurality of points thereof with coupling recesses such that, when the coupling protrusion is inserted into one of the coupling recesses, the switch member is fixed to the first rod, whereby the sliding of the switch member is stopped.

A plurality of coupling protrusions and a plurality of coupling recesses may be formed in a direction perpendicular to the sliding direction of the switch member.

At each position of the switch member at which the coupling protrusion on the switch member is inserted into one of the coupling recesses in the first rod, the switch member and the first rod may be provided with magnets, which face each other to attract each other.

The switch member may be provided at positions thereof spaced from the coupling protrusion with a plurality of magnets, which are disposed in the sliding direction of the switch member or a direction perpendicular to the sliding direction of the switch member, and the first rod may be provided at positions thereof corresponding to the magnets, which are provided at a plurality of points of the switch member at which the coupling protrusion on the switch member is inserted into each of the coupling recesses in the first rod, with magnets, which are disposed to face the respective magnets provided at the switch member to attract each other.

The switch member may include a body portion, on which the coupling protrusion is formed, and a rotation member rotatably coupled to the body portion, the rotation member having a first bearing formed at one end portion thereof, and when the rotation member is rotated relative to the body portion, the first bearing may be exposed in a direction in which the coupling protrusion protrudes, whereby the coupling protrusion may be separated from a corresponding one of the coupling recesses.

The other end portion of the rotation member may be exposed in a direction opposite to the direction in which the coupling protrusion protrudes, and when the other end portion of the rotation member is rotated relative to the body portion, the first bearing may rotate the body portion relative to the first rod while being exposed in the direction in which the coupling protrusion protrudes, whereby the coupling protrusion may be separated from the corresponding one of the coupling recesses.

The body portion may be provided with a support member protruding in the direction opposite to the direction in which the coupling protrusion protrudes, and the other end portion of the rotation member may extend to be disposed at an oblique angle relative to the support member such that, when the other end portion of the rotation member is pushed toward the support member, the rotation member is rotated relative to the body portion.

The second rod may be provided at one end portion thereof with a second bearing configured to be rotated such that the second rod slides along the first rod.

The second bearing may be coupled to the second rod to move in a pushing recess formed in one end portion of the second rod such that the second bearing is exposed out of the second rod toward the first rod or is inserted into the second rod, and the second rod may be provided with an elastic body for pushing the second bearing such that the second bearing is exposed out of the second rod toward the first rod in the pushing recess.

When the sliding of the second rod is stopped, one end portion of the second rod may come into contact with one side surface of the switch member to be supported thereby. One end portion of the second rod may be rounded, and one side surface of the switch member may have a shape that surrounds one end portion of the second rod.

In accordance with another aspect of the present invention, there is provided a wearable chair including the sliding stop switch according to an exemplary embodiment of the present invention described above, the wearable chair further including a third rod having an upper end portion rotatably coupled to one end portion of the first rod, the third rod extending in the longitudinal direction thereof, the third rod being rotatably coupled to the other end portion of the second rod, wherein, when the sliding of one end portion of the second rod is stopped at a point of the first rod by the switch member, the rotation of the second rod relative to the first rod or the third rod is stopped.

The first rod may be connected to the thigh of a user, and the third rod may be connected to the lower leg of the user, the lower end portion of the third rod being configured to contact the ground when the user sits down.

The methods and apparatuses of the present invention have other features and advantages which will be apparent from or are set forth in more detail in the accompanying drawings, which are incorporated herein, and the following Detailed Description, which together serve to explain certain principles of the present invention.

Figure 1:
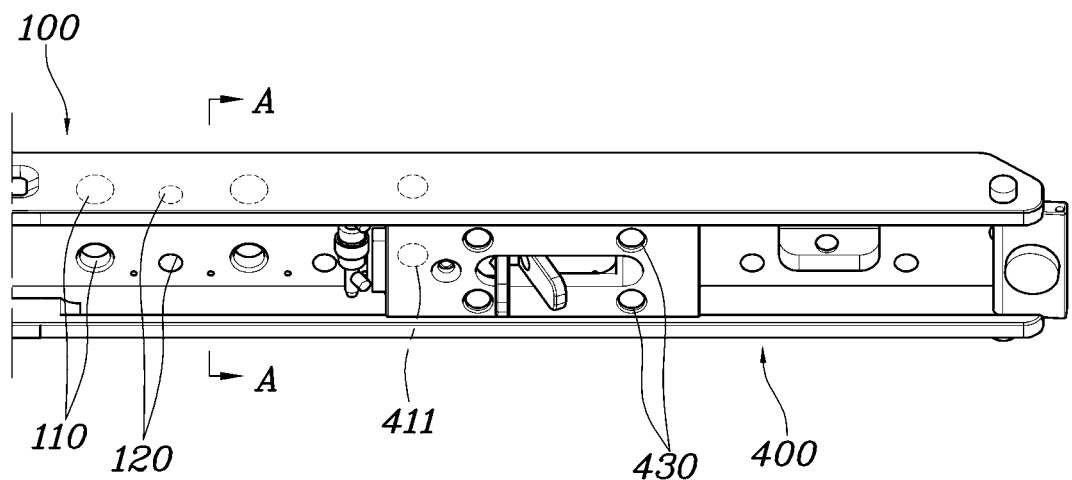
FIG. 1 is a perspective view showing the lower portion of a sliding stop switch according to an exemplary embodiment of the present invention.

It may be understood that the appended drawings are not necessarily to scale, presenting a somewhat simplified representation of various features illustrative of the basic principles of the present invention. The specific design features of the present invention as included herein, including, for example, specific dimensions, orientations, locations, and shapes will be determined in part by the particularly intended application and use environment.

In the figures, reference numbers refer to the same or equivalent parts of the present invention throughout the several figures of the drawing.

DETAILED DESCRIPTION

Reference will now be made in detail to various embodiments of the present invention(s), examples of which are illustrated in the accompanying drawings and described below. While the present invention(s) will be described in conjunction with exemplary embodiments of the present invention, it will be understood that the present description is not intended to limit the present invention(s) to those exemplary embodiments. On the other hand, the present invention(s) is/are intended to cover not only the exemplary embodiments of the present invention, but also various alternatives, modifications, equivalents and other embodiments, which may be included within the spirit and scope of the present invention as defined by the appended claims.

Specific structural or functional descriptions of the exemplary embodiments of the present invention disclosed in the present specification or this disclosure are provided only for illustrating embodiments of the present invention. Embodiments of the present invention may be realized in various forms, and should not be interpreted to be limited to the exemplary embodiments of the present invention disclosed in the present specification or this disclosure.

Since the exemplary embodiments of the present invention may be variously modified and may have various forms, specific embodiments will be shown in the drawings and will be described in detail in the present specification or this disclosure. the However, the exemplary embodiments according to the concept of the present invention are not limited to such specific embodiments, and it may be understood that the present invention may include all alterations, equivalents, and substitutes that fall within the idea and technical scope of the present invention.

It will be understood that, although the terms "first", "second", etc. may be used herein to describe various elements, corresponding elements may not be understood to be limited by these terms, which are used only to distinguish one element from another. For example, within the scope defined by the present invention, a first element may be referred to as a second element, and similarly, a second element may be referred to as a first element.

It will be understood that when a component is referred to as being "connected to" or "coupled to" another component, it may be directly connected to or coupled to the other component, or intervening components may be present. In contrast, when a component is referred to as being "directly connected to" or "directly coupled to" another component, there are no intervening components present. Other terms that describe the relationship between components, such as "between" and "directly between" or "adjacent to" and "directly adjacent to", must be interpreted in the same manner.

The terms used in the exemplary embodiment are provided only to explain specific embodiments, but are not intended to restrict the present invention. A singular representation may include a plural representation unless it represents a definitely different meaning from the context. It will be further understood that the terms "comprises", "has" and the like, when used in the exemplary embodiment, specify the presence of stated features, numbers, steps, operations, elements, components or combinations thereof, but do not preclude the presence or addition of one or more other features, numbers, steps, operations, elements, components, or combinations thereof.

Unless otherwise defined, all terms, including technical and scientific terms, used in the exemplary embodiment have the same meanings as those commonly understood by a person having ordinary skill in the art to which the present invention pertains. It will be further understood that terms, such as those defined in commonly used dictionaries, may be interpreted as having meanings consistent with their meanings in the context of the relevant art and the present invention, and are not to be interpreted in an idealized or overly formal sense unless so defined herein.

Reference will now be made in detail to the exemplary embodiments of the present invention, examples of which are illustrated in the accompanying drawings. Wherever possible, the same reference numbers will be used throughout the drawings to refer to the same or like parts.

Figure 2:
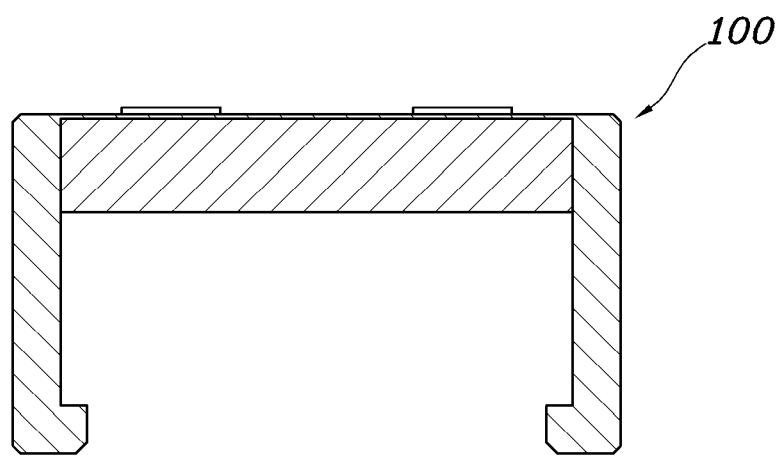
FIG. 2 is a sectional view taken along line A-A' of FIG. 1.
Figure 3:
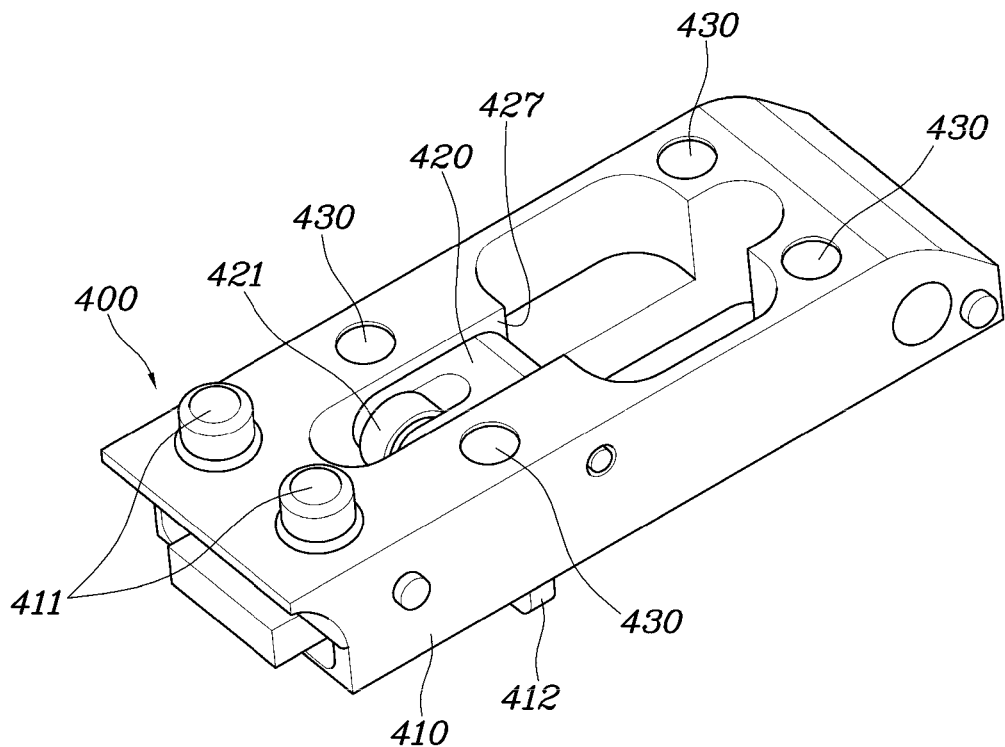
FIG. 3 is a perspective view showing a switch member according to an exemplary embodiment of the present invention.
Figure 4:
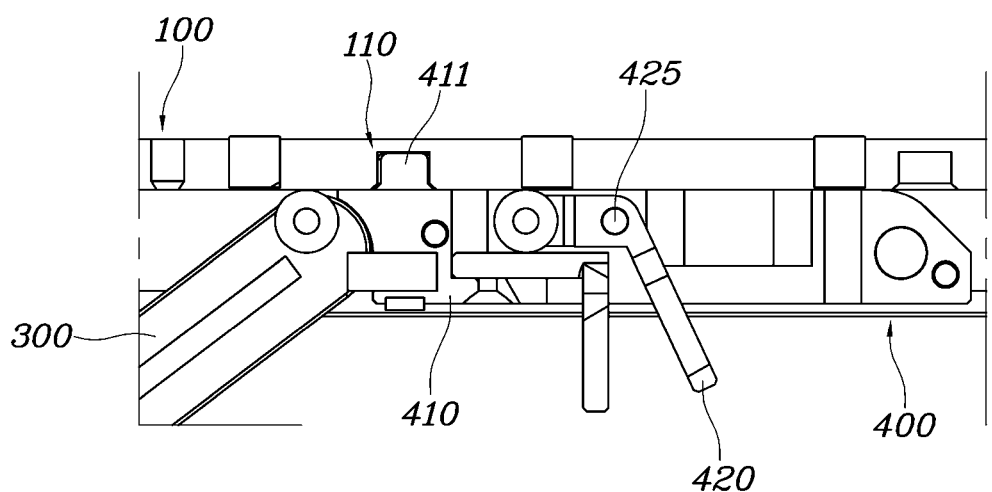
FIG. 4 is a sectional view showing the sliding stop switch according to the exemplary embodiment of the present invention.

FIG. 1 is a perspective view showing the lower portion of a sliding stop switch according to an exemplary embodiment of the present invention, FIG. 2 is a sectional view taken along line A-A' of FIG. 1, FIG. 3 is a perspective view showing a switch member according to an exemplary embodiment of the present invention, and FIG. 4 is a sectional view showing the sliding stop switch according to the exemplary embodiment of the present invention.

Referring to FIGS. 1 to 4, the sliding stop switch according to the exemplary embodiment of the present invention includes a first rod 100 extending in the longitudinal direction thereof, a second rod 300 coupled to the first rod 100 such that one end portion thereof is slidable in the longitudinal direction of the first rod 100, and a switch member 400 coupled to the first rod 100 to slide in the longitudinal direction of the first rod 100 and to be fixed at a plurality of points on the first rod 100 to stop sliding of one end portion of the second rod 300.

The second rod 300 is coupled to the first rod 100 such that one end portion thereof is slidable in the longitudinal direction of the first rod 100. The switch member 400 is also slidably coupled to the first rod 100. Furthermore, the switch member 400 is coupled to the first rod 100 to be fixed at a plurality of points on the first rod 100 in the longitudinal direction of the first rod 100. When the switch member 400 is fixed at one of the points on the first rod 100, the sliding of the second rod 300 in the longitudinal direction of the first rod 100 is stopped.

In particular, further sliding of the second rod 300 is stopped in the state in which one end portion of the second rod 300 is in contact with one side surface of the switch member 400. Even in the case in which one end portion of the second rod 300 pushes one side surface of the switch member 400, therefore, the sliding of the second rod 300 is stopped by the fixed switch member 400.

That is, the switch member 400 is fixed while sliding in the longitudinal direction of the first rod 100 to stop the sliding of the second rod 300 at a plurality of points.

The first rod 100 may be located on the second rod 300 or the switch member 400 to surround opposite side surfaces and a portion of the lower surface of the second rod 300 or the switch member 400.

The second rod 300 and the switch member 400 are slidably coupled to the first rod 100 thereunder. The first rod 100 may have a shape that surrounds the upper portion, opposite side surfaces, and a portion of the lower surface of each of the second rod 300 and the switch member 400. That is, the first rod 100 may prevent the second rod 300 and the switch member 400 from moving further downwards under the first rod 100. Consequently, the second rod 300 and the switch member 400 are prevented from being separated downwards from the first rod 100.

When the sliding of the second rod 300 is stopped, one end portion of the second rod 300 comes into contact with one side surface of the switch member 400 to be supported thereby. One end portion of the second rod 300 may be rounded, and one side surface of the switch member 400 may have a shape that surrounds one end portion of the second rod 300. Consequently, the pressure of the switch member 400 which is applied to the second rod 300 may be dispersed.

One side surface of the switch member 400 may extend toward the first rod 100 to surround the rounded end portion of the second rod 300 on the first rod side thereof. Even in the case in which one side surface of the switch member 400 is pushed by the second rod 300, therefore, the switch member 400 may be pushed toward the first rod 100. Consequently, the switch member 400 is prevented from moving away from the first rod 100, whereby the state in which the switch member 400 is fixed to the first rod 100 is not released.

The switch member 400 is provided at one side thereof with a coupling protrusion 411, which protrudes toward the first rod 100, and the first rod 100 is provided at a plurality of points thereof with coupling recesses 110. When the coupling protrusion 411 is inserted into one of the coupling recesses 110, therefore, the switch member 400 may be fixed to the first rod 100, whereby the sliding of the switch member 400 may be stopped.

That is, when the coupling protrusion 411 on the switch member 400 is inserted into one of the coupling recesses 110 in the first rod 100, the switch member 400 is fixed to the first rod 100, and when the coupling protrusion 411 is separated from the coupling recess 110, the switch member 400 may slide in the longitudinal direction of the first rod 100. Consequently, the switch member 400, which stops the sliding of the second rod 300, is securely fixed while the position thereof is easily variable.

The coupling protrusion 411 may be located only at one side of the switch member 400 to be separated from the coupling recess 110 when the switch member 400 is rotated. A plurality of coupling recesses 110 may be disposed in a direction parallel to the longitudinal direction of the first rod 100 and to the sliding direction of the switch member 400 such that the coupling protrusion 411 is coupled to a plurality of points disposed in the longitudinal direction of the first rod 100.

A plurality of coupling protrusions 411 and a plurality of coupling recesses 110 may be formed in a direction perpendicular to the sliding direction of the switch member 400. That is, the coupling protrusions 411 and the coupling recesses 110 may be coupled to each other at a plurality of points in a direction perpendicular to the sliding direction of the switch member 400, whereby the force of coupling therebetween is increased, and the coupling protrusions 411 and the coupling recesses 110 are prevented from being rotated about the direction in which the coupling protrusions protrude or about the direction in which the coupling recesses are recessed.

At the positions of the switch member 400 at which the coupling protrusions 411 on the switch member 400 are inserted into the coupling recesses 110 in the first rod 100, the switch member 400 and the first rod 100 may be provided with magnets 430 and 120, which face each other to attract each other. The switch member 400 and the first rod 100 may have permanent magnets disposed such that N poles and S poles thereof face each other to attract each other.

The magnets 430 and 120, which are provided at the switch member 400 and the first rod 100, respectively, have relatively low attractive force, the attractive force being necessary to guide the coupling protrusions 411 on the switch member 400 toward the coupling recesses 110 in the first rod 100 such that the coupling protrusions 411 are inserted into the coupling recesses 110. That is, the attractive force of the magnets 430 and 120 is used to locate the switch member 400 at a predetermined position such that the coupling protrusions 411 are inserted into the coupling recesses 110, which are spaced from each other. Consequently, the switch member 400 is guided to the predetermined position such that the switch member 400 is easily fixed to the first rod 100.

The switch member 400 may be provided at positions thereof spaced from the coupling protrusions 411 with a plurality of magnets 430, which are disposed in the sliding direction of the switch member 400 or a direction perpendicular to the sliding direction of the switch member 400, and the first rod 100 may be provided at the positions thereof corresponding to the magnets 430, which are provided at a plurality of points of the switch member 400 at which the coupling protrusions 411 on the switch member 400 are inserted into the coupling recesses 110 in the first rod, with magnets 120, which are disposed to face the respective magnets 430 to attract each other.

To prevent the attractive force of the magnets 430 from impeding the separation of the coupling protrusions 411 from the respective coupling recesses 110, the magnets 430 may be located to be spaced from the coupling protrusions 411. The magnets 430 are spaced from each other such that the switch member 400 is stably supported by the first rod 100 due to the attractive force of the magnets.

Furthermore, as shown, the switch member 400 may be provided with two magnets 430 spaced from each other in the sliding direction thereof, and the coupling recesses 110 may be formed in the first rod 100 to be spaced from each other with a predetermined distance. At positions of the switch member 400 at which the coupling protrusions 411 on the switch member 400 are inserted into the coupling recesses 110 in the first rod, the magnets 120 may be provided at the first rod, and the magnets 120 provided at the first rod may be disposed at the same interval such that some of the magnets overlap each other.

Furthermore, a plurality of magnets 430 may be disposed at the switch member 400 in a direction perpendicular to the sliding direction of the switch member. Consequently, the position of the switch member 400 is stably guided due to the attractive force of the magnets.

Figure 5A:
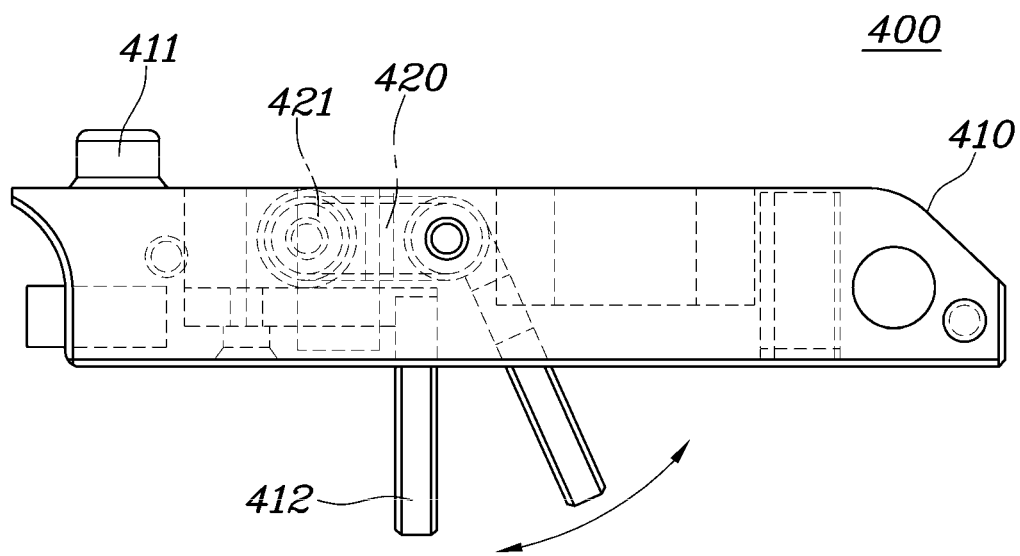
FIG. 5A and FIG. 5B are views showing the state in which the switch member according to the exemplary embodiment of the present invention is rotated.
Figure 5B:
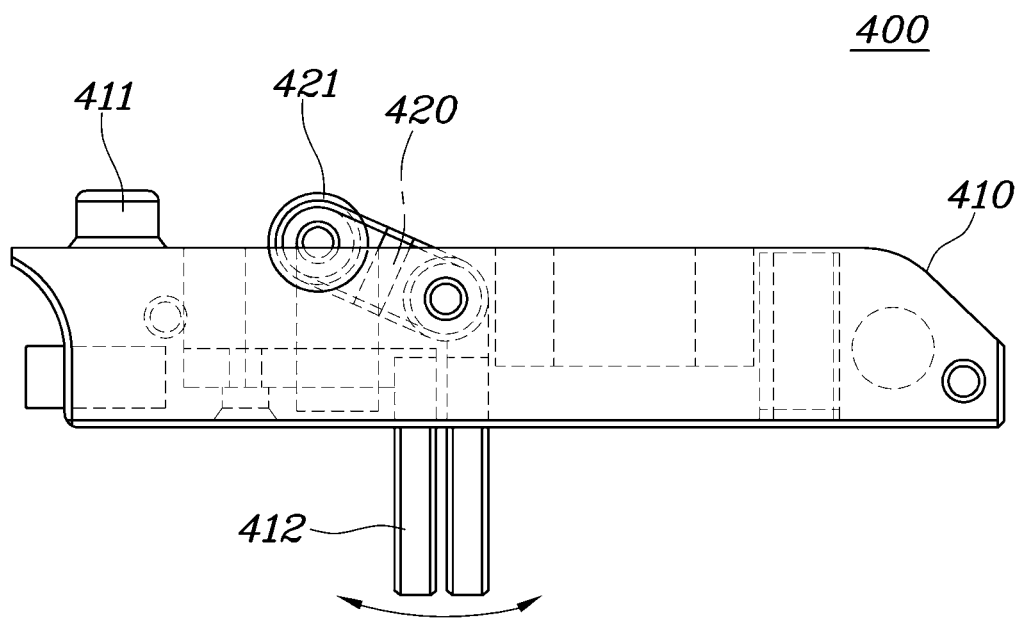
Figure 6:
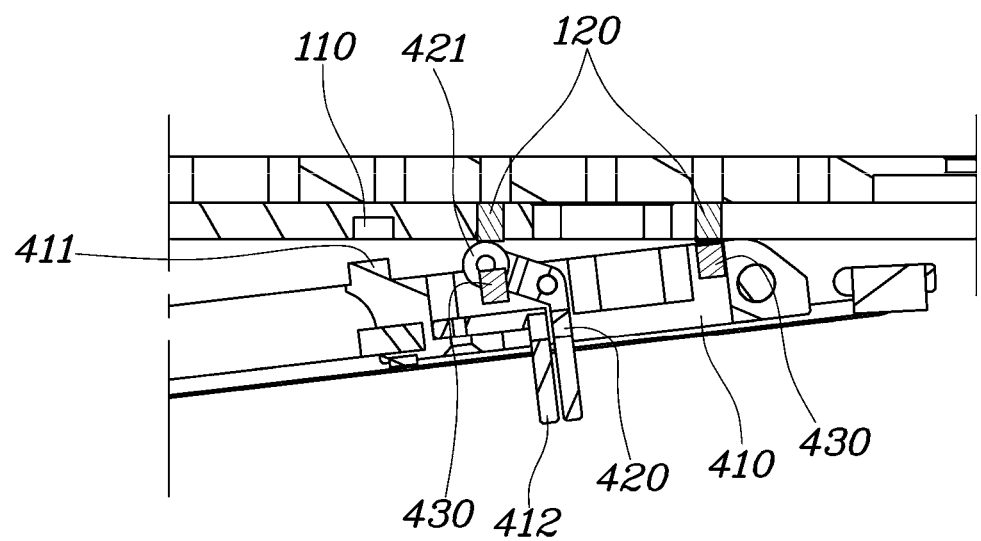
FIG. 6 is a sectional view showing the state in which fixation of the switch member according to the exemplary embodiment of the present invention is released.

FIG. 5A and FIG. 5B are views showing the state in which the switch member 400 according to the exemplary embodiment of the present invention is rotated, and FIG. 6 is a sectional view showing the state in which fixation of the switch member 400 according to the exemplary embodiment of the present invention is released.

Further referring to FIGS. 5A, 5B, and 6, the switch member 400 includes a body portion 410, on which the coupling protrusions 411 are formed, and a rotation member 420 rotatably coupled to the body portion 410, the rotation member 420 having a first bearing 421 formed at one end portion thereof. When the rotation member 420 is rotated relative to the body portion 410, the first bearing 421 is exposed in the direction in which the coupling protrusions 411 protrude, whereby the coupling protrusions 411 may be separated from the coupling recesses 110.

The other end portion of the rotation member 420 is exposed in the direction opposite to the direction in which the coupling protrusions 411 protrude, and when the other end portion of the rotation member 420 is rotated relative to the body portion 410, the first bearing 421 rotates the body portion 410 relative to the first rod 100 while being exposed in the direction in which the coupling protrusions 411 protrude, whereby the coupling protrusions 411 may be separated from the coupling recesses 110.

Furthermore, a support member 412, protruding in the direction opposite to the direction in which the coupling protrusions 411 protrude, is formed at the body portion 410, and the other end portion of the rotation member 420 extends to be disposed at an oblique angle relative to the support member. When the other end portion of the rotation member 420 is pushed toward the support member, therefore, the rotation member 420 may be rotated relative to the body portion 410.

That is, the switch member 400 may include a body portion 410 and a rotation member 420, which are rotatably coupled to each other via a hinge 425. When no external force is applied, the body portion 410 is disposed parallel to the sliding direction of the switch member due to the attractive force of the magnets 430 and 120, whereby the coupling protrusions 411 remain inserted into the coupling recesses 110, and the first bearing 421, formed at one end portion of the rotation member 420, remains inserted into a receiving hole 427 of the body portion 410.

When the other end portion of the rotation member 420, formed to be disposed at an oblique angle relative to the support member 412, is pushed toward the coupling protrusions 411, the first bearing 421, formed at one end portion of the rotation member 420, may be exposed toward the coupling protrusions 411 on the body portion 410 at the supporting point at which the rotation member 420 is hingedly coupled to the body portion 410 according to the principle of a lever. As a result, the first bearing 421 causes relative rotation between the body portion 410 and the rotation member 420 in the state of being supported by the lower surface of the first rod 100. The first bearing 421 is rotated toward the side of the switch member 400 opposite to the side of the switch member 400 at which the coupling protrusions 411 are formed such that the coupling protrusions 411 on the body portion 410 are separated from the coupling recesses 110.

Consequently, the other end portion of the rotation member 420 is easily rotated by pushing the other end portion of the rotation member 420 and the support member at opposite sides thereof, whereby the coupling protrusions 411 on the body portion 410 are separated from the coupling recesses 110, and therefore the fixation of the switch member 400 is easily released.

Figure 7A:
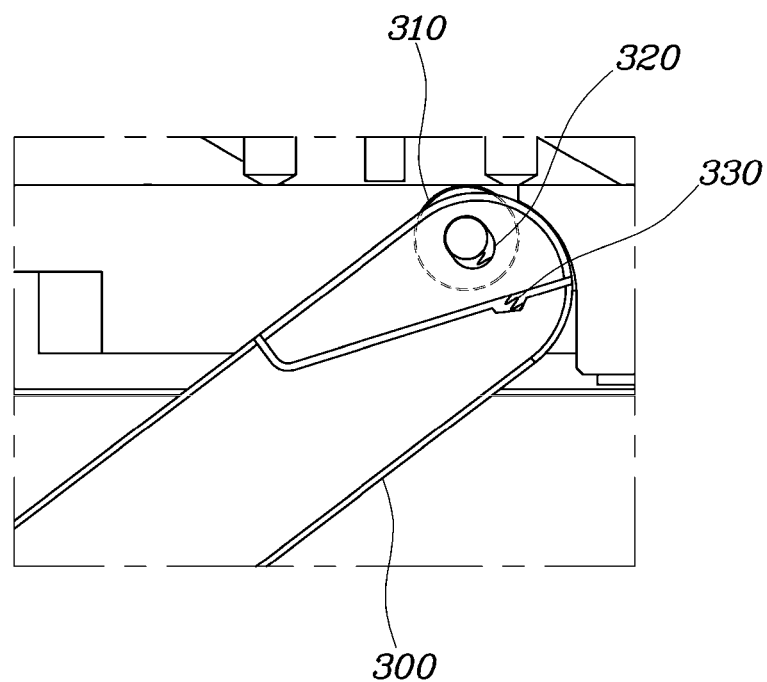
FIG. 7A and FIG. 7B are views showing the state in which a second bearing according to an exemplary embodiment of the present invention is moved in a pushing recess.
Figure 7B:
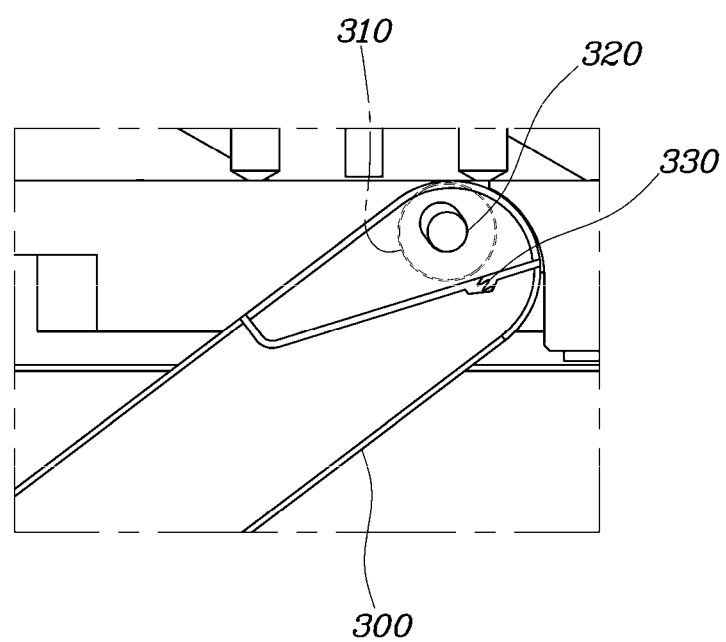

FIG. 7A and FIG. 7B are views showing the state in which a second bearing 310 according to an exemplary embodiment of the present invention is moved in a pushing recess 320.

Referring to FIG. 7A and FIG. 7B, a second bearing 310, configured to be rotated such that the second rod 300 slides along the first rod 100, may be formed at one end portion of the second rod 300. The second bearing 310, formed at one end portion of the second rod 300, which slides in the longitudinal direction of the first rod 100, is rotated in the state of being in contact with the lower surface of the first rod 100, whereby the second rod 300 slides. Consequently, it is possible to smoothly slide the second rod 300.

The second bearing 310 may be coupled to the second rod 300 to move in a pushing recess 320 formed in one end portion of the second rod 300 such that the second bearing 300 is exposed out of the second rod 300 toward the first rod 100 or is inserted into the second rod 300, and the second rod 300 may be provided with an elastic body 330 for pushing the second bearing 310 such that the second bearing 300 is exposed out of the second rod 300 toward the first rod 100 in the pushing recess 320.

When no external force is applied, therefore, the second bearing 310 may be exposed out of the second rod 300 toward the first rod 100 due to the elastic force of the elastic body 330, whereby the second bearing 310 may remain in contact with the lower surface of the first rod 100. When external force greater than the elastic force of the elastic body 330 is applied, however, the second bearing 310 may move relative to the second rod 300 in the pushing recess 320, whereby the second bearing 310 may be inserted into the second rod 300. In the case in which excessive compressive force is applied to the second rod 300, therefore, the second bearing 310 is inserted into the second rod 300 such that the applied force is not concentrated on the second bearing 310, whereby it is possible to prevent damage to the second bearing 310.

Figure 8:
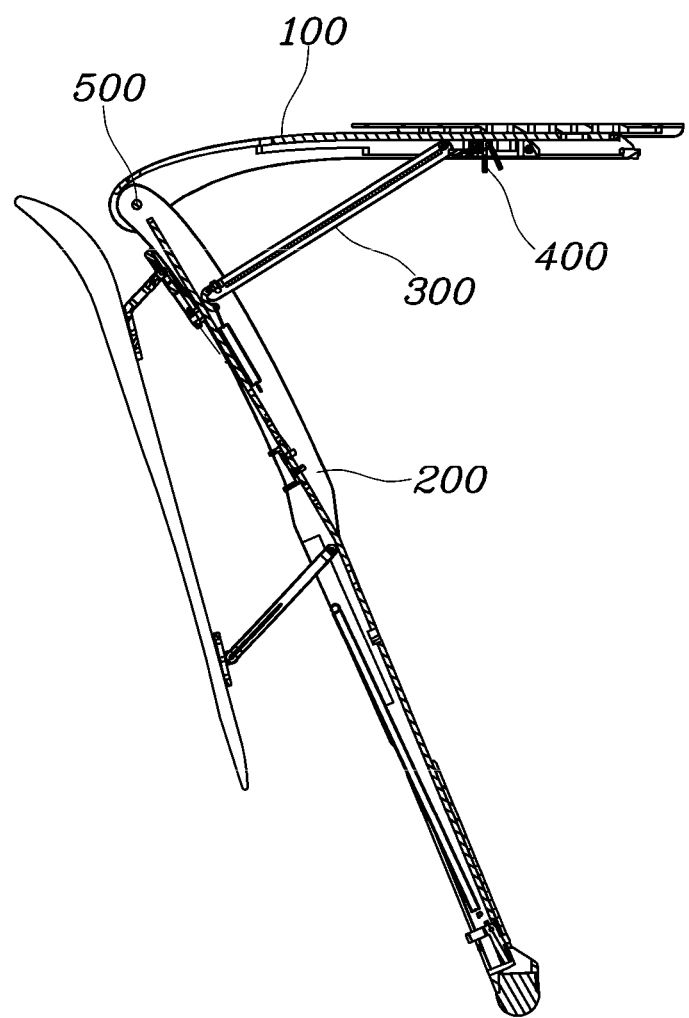
FIG. 8 is a sectional view showing a wearable chair including the sliding stop switch according to the exemplary embodiment of the present invention.

FIG. 8 is a sectional view showing a wearable chair including the sliding stop switch according to the exemplary embodiment of the present invention.

Referring to FIG. 8, the wearable chair further includes a third rod 200 having an upper end portion rotatably coupled to one end portion of the first rod 100, the third rod 200 extending in the longitudinal direction thereof, the third rod 200 being rotatably coupled to the other end portion of the second rod 300, in addition to the sliding stop switch according to the exemplary embodiment of the present invention. When the sliding of one end portion of the second rod 300 is stopped at a point of the first rod 100 by the switch member 400, the rotation of the second rod 300 relative to the first rod 100 or the third rod 200 may be stopped.

The first rod 100 may be connected to the thigh of a user, and the third rod 200 may be connected to the lower leg of the user. The lower end portion of the third rod 200 may contact the ground when the user sits down.

The first rod 100, which is coupled to the rear of the thigh of the user, and the third rod 200, which is coupled to the rear of the lower leg of the user, are rotatably coupled to each other via a hinge 500. The second rod 300, one end portion of which is slidably coupled to the first rod 100 and the other end portion of which is rotatably coupled to the third rod 200, is rotated relative to the second rod 300 while sliding along the first rod 100 when the first rod 100 and the third rod 200 are rotated relative to each other.

In the case in which the switch member 400 is fixed to the first rod 100, whereby one side surface of the switch member 400 contacts the third rod 200 to stop the sliding of the third rod 200, the sliding of the third rod 200 along the first rod 100 is stopped, whereby the first rod 100 and the second rod 300 are prevented from being rotated relative to each other. That is, when the user sits down in the state of wearing the wearable chair, the first rod 100 and the third rod 200, which correspond to the thigh and the lower leg of the user, respectively, are not rotated relative to each other any Furthermore, whereby the weight of the user may be supported by the second rod 300.

Furthermore, the fixed position of the switch member 400 may be changed along the first rod 100, whereby it is possible to easily change a sitting angle.

As is apparent from the above description, the sliding stop switch according to an exemplary embodiment of the present invention has an effect in that the switch member, which stops the sliding of the second rod, is securely fixed while the position thereof is easily variable.

Furthermore, the wearable chair including the sliding stop switch according to an exemplary embodiment of the present invention has an effect in that the fixed position of the switch member is changed along the first rod, whereby it is possible to easily change a sitting angle.

For convenience in explanation and accurate definition in the appended claims, the terms "upper", "lower", "inner", "outer", "up", "down", "upper", "lower", "upwards", "downwards", "front", "rear", "back", "inside", "outside", "inwardly", "outwardly", "internal", "external", "inner", "outer", "forwards", and "backwards" are used to describe features of the exemplary embodiments with reference to the positions of such features as displayed in the figures.

It will be further understood that the term "connect" or its derivatives refer both to direct and indirect connection.

The foregoing descriptions of specific exemplary embodiments of the present invention have been presented for purposes of illustration and description. They are not intended to be exhaustive or to limit the present invention to the precise forms disclosed, and obviously many modifications and variations are possible in light of the above teachings. The exemplary embodiments were chosen and described to explain certain principles of the present invention and their practical application, to enable others skilled in the art to make and utilize various exemplary embodiments of the present invention, as well as various alternatives and modifications thereof. It is intended that the scope of the present invention be defined by the Claims appended hereto and their equivalents.

What is claimed is:

1. A sliding stop switch apparatus comprising:
   a first rod extending in a longitudinal direction thereof;
   a second rod slidably coupled to the first rod such that a first end portion of the second rod is slidable in the longitudinal direction of the first rod; and
   a switch member slidably coupled to the first rod to slide in the longitudinal direction of the first rod and configured to be selectively fixed at at least one of a plurality of points on the first rod to stop sliding of the first end portion of the second rod in the first rod,
   wherein the switch member is provided at a side thereof with a coupling protrusion formed protrudingly toward the first rod, and the first rod is provided at the plurality of points with coupling recesses such that, when the coupling protrusion is inserted into at least one of the coupling recesses, the switch member is fixed to the first rod, whereby sliding of the switch member is stopped by the coupling protrusion, and
   wherein, at each position of the switch member at which the coupling protrusion on the switch member is inserted into one of the coupling recesses in the first rod, the switch member and the first rod are respectively provided with a first magnet and a second magnet, which face each other to attract each other.

2. The sliding stop switch apparatus according to claim 1, wherein the first rod is located on the second rod or the switch member to surround opposite side surfaces and a portion of a lower surface of the second rod or the switch member.

3. The sliding stop switch apparatus according to claim 1, wherein the coupling protrusion is formed of a plurality of coupling protrusions and the coupling recesses are formed in a direction perpendicular to a sliding direction of the switch member.

4. The sliding stop switch apparatus according to claim 1, wherein the switch member is provided at positions thereof spaced from the coupling protrusion with a plurality of first magnets, which are mounted in a sliding direction of the switch member or a direction perpendicular to the sliding direction of the switch member, and
wherein the first rod is provided at positions thereof corresponding to the plurality of first magnets, which are provided at the plurality of points of the switch member at which the coupling protrusion on the switch member is inserted into each of the coupling recesses in the first rod, with a plurality of second magnets, which are mounted to face the respective first magnets provided at the switch member to attract each other.

5. The sliding stop switch apparatus according to claim 1, wherein the switch member includes a body portion, on which the coupling protrusion is formed, and a rotation member pivotally coupled to the body portion in a receiving hole formed in the body portion of the switch member, the rotation member having a first bearing mounted at a first end portion of the rotation member, and
wherein, when the rotation member is rotated relative to the body portion, the first bearing is exposed in a direction in which the coupling protrusion protrudes, whereby the coupling protrusion is separated from a corresponding one of the coupling recesses.

6. The sliding stop switch apparatus according to claim 5, wherein a second end portion of the rotation member is exposed through the receiving hole in a direction opposite to the direction in which the coupling protrusion protrudes, and
wherein when the second end portion of the rotation member is rotated relative to the body portion, the first bearing rotates the body portion relative to the first rod while being exposed in the direction in which the coupling protrusion protrudes, whereby the coupling protrusion is separated from the corresponding one of the coupling recesses.

7. The sliding stop switch apparatus according to claim 6, wherein the body portion is provided with a support member protruding in the direction opposite to the direction in which the coupling protrusion protrudes, and the second end portion of the rotation member extends to be disposed through the receiving hole at an oblique angle relative to the support member such that, when the second end portion of the rotation member is pushed toward the support member, the first end portion of the rotation member is rotated relative to the body portion toward the first rod.

8. The sliding stop switch apparatus according to claim 1, wherein the second rod is provided at the first end portion thereof with a second bearing configured to be rotated such that the second rod slides along the first rod.

9. The sliding stop switch apparatus according to claim 8, wherein the second bearing is slidably coupled to a pushing recess formed in the first end portion of the second rod to move in the pushing recess such that the second bearing is exposed out of the second rod toward the first rod or is moved inward the second rod, and
wherein the first end portion of the second rod is provided with an elastic body for pushing the first end portion of the second bearing outward the second rod such that the second bearing is selectively exposed by the elastic body out of the second rod toward the first rod in the pushing recess.

10. The sliding stop switch apparatus according to claim 1, wherein when the sliding of the second rod is stopped, the first end portion of the second rod comes into contact with a side surface of the switch member to be supported thereby.

11. The sliding stop switch apparatus according to claim 1, wherein the first end portion of the second rod is rounded and a side surface of the switch member has a shape that surrounds the first end portion of the second rod.

12. A wearable chair comprising:
the sliding stop switch apparatus according to claim 1; and
a third rod having an upper end portion rotatably coupled to an end portion of the first rod, the third rod extending in a longitudinal direction thereof,
wherein the third rod is rotatably coupled to a second end portion of the second rod.

13. The wearable chair according to claim 12, wherein the first rod is configured to be connected to a thigh of a user,
wherein the third rod is configured to be connected to a lower leg of the user, and
wherein a lower end portion of the third rod is configured to contact a ground when the user sits down.

14. The wearable chair according to claim 12, wherein when sliding of the first end portion of the second rod is stopped at a point of the first rod by the switch member, a rotation of the second rod relative to the first rod or the third rod is stopped.

* * * * *